(12) United States Patent
Zerfass et al.

(10) Patent No.: US 12,086,960 B2
(45) Date of Patent: *Sep. 10, 2024

(54) CROSS-TALK COMPENSATION (71) Applicant: QIAGEN GmbH, Hilden (DE)

(72) Inventors: Thorsten Zerfass, Mühleim an der Ruhr (DE); Maiko Lohel, Hilden (DE); Fernando Carrillo Oesterreich, Düsseldorf (DE)

(73) Assignee: QIAGEN GmbH, Hilden (DE)

( * ) Notice: Subject to any disclaimer, the term of this patent is extended or adjusted under 35 U.S.C. 154(b) by 441 days.

This patent is subject to a terminal disclaimer.

(21) Appl. No.: 17/215,956

(22) Filed: Mar. 29, 2021

(65) Prior Publication Data

US 2021/0390666 A1    Dec. 16, 2021

Related U.S. Application Data (63) Continuation of application No. 16/344,912, filed as application No. PCT/EP2017/076826 on Oct. 20, 2017, now Pat. No. 10,963,992.

(30) Foreign Application Priority Data

Oct. 25, 2016   (EP) .................................... 16195545

(51) Int. Cl.
*G06T 5/70* (2024.01)
*G01N 21/64* (2006.01)
(Continued)

(52) U.S. Cl.
CPC ........... *G06T 5/70* (2024.01); *G01N 21/6428* (2013.01); *G01N 21/6456* (2013.01); *G06T 5/92* (2024.01);
(Continued)

(58) Field of Classification Search
CPC ........... G06T 5/002; G06T 5/009; G06T 7/00; G06T 2207/6441; G06T 2207/10064;
(Continued)

(56) References Cited

U.S. PATENT DOCUMENTS 5,866,331 A     2/1999  Singer et al.
10,963,992 B2 *  3/2021  Zerfass .............. G01N 21/6456
(Continued)

FOREIGN PATENT DOCUMENTS

CN           102482720 A    5/2012
WO     WO 2008/097455 A1    8/2008
(Continued)

OTHER PUBLICATIONS

International Search Report and Written Opinion of the International Searching Authority directed to related International Patent Application No. PCT/EP2017/076826, dated Jan. 16, 2019; 15 pages.
(Continued)

*Primary Examiner* — Michael R Neff
(74) *Attorney, Agent, or Firm* — Sterne, Kessler, Goldstein & Fox P.L.L.C.

(57) ABSTRACT

Method and system for compensating intensity biases in a plurality of digital images. Each digital image of the plurality of digital images contains a plurality of objects and each of the plurality of objects is configured to receive at least one molecule comprising genetic information, wherein the at least one molecule is configured to receive one of at least a first fluorescent compound and a second fluorescent compound. A first digital image of the plurality of digital images is taken by an optical imaging system during emission of electromagnetic radiation by the first fluorescent compound, and a second digital image of the plurality of digital images is taken by the optical imaging system during
(Continued)

emission of electromagnetic radiation by the second fluorescent compound.

17 Claims, 5 Drawing Sheets

(51) Int. Cl.
    *G06T 5/92*     (2024.01)
    *G06T 7/00*     (2017.01)
    *G16B 30/00*     (2019.01)
    *G16B 40/00*     (2019.01)
    *G16B 40/10*     (2019.01)
    *C12Q 1/6869*     (2018.01)

(52) U.S. Cl.
    CPC ............... *G06T 7/00* (2013.01); *G16B 30/00* (2019.02); *G16B 40/00* (2019.02); *G16B 40/10* (2019.02); *C12Q 1/6869* (2013.01); *G01N 2021/6441* (2013.01); *G06T 2207/10064* (2013.01); *G06T 2207/20208* (2013.01); *G06T 2207/30072* (2013.01)

(58) Field of Classification Search
    CPC .......... G06T 2207/20208; G06T 2207/30072; G16B 40/00; G16B 40/10; G16B 30/00; G01N 21/6428; G01N 21/6456; G01N 2021/6441; C12Q 1/6869
    USPC ....................................................... 382/128
    See application file for complete search history.

(56) References Cited

U.S. PATENT DOCUMENTS

| | | |
|---|---|---|
| 2003/0175720 A1 | 9/2003 | Bozinov et al. |
| 2003/0179948 A1 | 9/2003 | Gindele |
| 2010/0323350 A1 | 12/2010 | Gordon et al. |
| 2014/0057255 A1* | 2/2014 | Holmes ................. G01N 21/07 435/6.12 |
| 2014/0106469 A1 | 4/2014 | Wu et al. |
| 2014/0119595 A1 | 5/2014 | Gallo et al. |
| 2014/0187931 A1 | 7/2014 | Wood et al. |
| 2015/0177148 A1 | 6/2015 | Estrada |
| 2021/0150715 A1* | 5/2021 | Garcia ................... G06T 7/246 |

FOREIGN PATENT DOCUMENTS

| | | |
|---|---|---|
| WO | WO 2009/117119 A1 | 9/2009 |
| WO | WO 2014/020137 A1 | 2/2014 |

OTHER PUBLICATIONS

International Preliminary Report on Patentability directed to related International Patent Application No. PCT/EP2017/076826, dated Apr. 30, 2019; 11 pages.

Li et al., "An estimate of the crosstalk matrix in four-dye fluorescence-based DNA sequencing," Electrophoresis, vol. 20, No. 7, Jun. 1999, pp. 1433-1442.

Metzker, M.L., "Sequencing technologies—the next generation," Nat. Rev. Genetics, vol. 11, No. 1, Jan. 2010, pp. 31-46.

Voelkerding et al., "Next-generation sequencing: From basic research to diagnostics," Clinical Chemistry, vol. 55, No. 4, Apr. 2009, pp. 641-658.

Wang et al., "Achieving Accurate and Fast Base-calling by a Block Model of the Illumina Sequencing Data," IFAC Symposium, vol. 48, No. 28, Oct. 2015, pp. 1462-1465.

Whiteford et al., "Swift: primary data analysis for the Illumina Solexa sequencing platform," Bioinformatics, vol. 25, No. 17, Sep. 1, 2009, pp. 2194-2199.

Yin et al., "Automatic Matrix Determination in Four Dye Flourescence-Based DNA Sequencing," Electrophoresis, vol. 17, No. 6, Jun. 1996, pp. 1143-1150.

Cui, Q. et al., "Supercontiuum for Multicolor Two-photon Microscopy," Acta Laser Biology Sinica, vol. 24, No. 1, pp. 1-7 and 16, Feb. 2015.

* cited by examiner

CROSS-TALK COMPENSATION

CROSS-REFERENCE TO RELATED APPLICATIONS

This application is a continuation of U.S. application Ser. No. 16/344,912, filed Apr. 25, 2019, now allowed, which claims priority to International Patent Application No. PCT/EP2017/076826, now expired, each of which is incorporated herein by reference in its entirety.

SUMMARY

The present invention relates to systems and methods for cross-talk compensation. More particularly, the present invention relates to cross-talk compensation of electromagnetic radiation emitted by different fluorescent compounds in different color channels, preferably for DNA-sequencing.

Biotechnology, medicine and related technical fields are based on the analysis of molecules. Electronic devices can analyze molecules with high precision and specificity. Especially in last years, automated electronic devices have been developed for analyzing large numbers of samples by routine methods. For example, modern DNA sequencing apparatus are used for routine analysis of large numbers of DNA probes. Protein samples can be analyzed by high throughput screening and related methods. Frequently, such electronic devices detect fluorescent signals emitted from the sample probes. This is possible when molecules, such as nucleic acids or proteins, have been labeled with fluorescent compounds such as dyes.

Commercially available sequencing apparatus are capable of sequencing large numbers of samples labeled with fluorescent dyes in parallel. Recently developed methods, referred to as "next-generation sequencing", NGS, have revolutionized sequencing. For example, NGS allows massively parallel sequencing of local clusters of identical DNA molecules. Formation of these clusters are realized by clonal DNA amplification of template DNA molecules on the flow cell (OFCA, on flow cell amplification) or by immobilization of beads carrying clonal DNA molecules, amplified by emulsion PCR (polymerase chain reaction). NGS allows thousands or even millions to billions of sequencing reactions to be performed simultaneously.

In NGS, sequencing is performed by repeated cycles of polymerase-mediated nucleotide extensions or by iterative cycles of oligonucleotide ligation. As a massively parallel process, NGS generates hundreds of megabases to gigabases of nucleotide-sequence output in a single instrument run, depending on the platform. Compared to other methods, NGS may allow i) the inexpensive production of large volumes of sequence data, ii) may have low requirements for the amount of starting material and iii) may allow, at least in theory, the quantification of all DNA molecules in a sample. It may therefore replace conventional sequencing methods for many applications.

NGS platforms and common applications/fields for NGS technologies are e.g. reviewed in Voelkerding et al, Clinical Chemistry 55:4 641-658, 2009 and Metzker, Nature Reviews/Genetics Volume 11, January 2010, pages 31-46.

In NGS, various oligonucleotides of interest are covalently attached to a support. Subsequently, a nucleotide labeled with a fluorescent dye is attached to the growing oligonucleotide chain with DNA polymerase. When the four nucleotides are labeled with different fluorescent dyes, fluorescent signals emitted from a probe can be detected and the type of nucleotide attached to the oligonucleotide can be identified. After detection, the fluorescent dye is cleaved off and the next synthesis cycle is carried out, in which a new labeled nucleotide is attached to the growing chain. By carrying out multiple cycles, the sequence of a growing oligonucleotide chain can be determined in a stepwise manner. The working steps are carried out in an automated sequencing apparatus.

US 2010/0323350 A1 and WO 2009/117119 A1 relate to methods and compositions for determining the identity of nucleic acids in nucleotide sequences using, for example, data obtained from sequencing by synthesis methods.

WO 2008/097455 A1 relates to an imaging system for exciting and measuring fluorescence on or in samples comprising fluorescent materials, e.g. fluorescent labels, dyes or pigments, in particular to detect fluorescent labels on nucleic acid. Moreover, a device is disclosed being configured such that fluorescent labels in a plurality of different DNA templates are simultaneously detected.

WO 2014/020137 A1 relates to a method for enriching target sequences from a sequencing library to provide a target enriched sequencing library, wherein the sequencing library is suitable for massive parallel sequencing and comprises a plurality of double-stranded nucleic acid molecules.

Fluorescent signals emitted from sample probes with labeled molecules are weak, but the signals have to be detected with high precision and specificity. Thus, precise optical equipment, especially cameras and scanning technology, is required for such processes.

In addition, extensive evaluation of the digital images captured by an optical imaging system of the sequencing apparatus is necessary for obtaining a precise and reliable result of the sequencing, e.g. in FASTQ.

Channel intensities may be used as proxies for the concentration of underlying fluorescently labeled molecules. Ideally, channel-specific intensities may be identically distributed and independent of each other (iid). This, however, is often not the case: Distinct imaging properties can lead to different intensity distribution for each channel. A) Different fluorescent dyes can have an overlap in their emission frequencies. This may lead to a higher than background intensity level in a fluorophore-specific channel without the fluorophore being present. This interdependence of bead intensity values may be denoted as cross-talk or cross-correlation. B) Channel specific background fluorescence may lead to different levels of minimal observed values (noise offset). C) Channel specific brightness may lead to different intensity values in different channels for the same underlying fluorophore concentration (channel scaling). All three phenomena can lead to a deviation from the simple (linear) relationship of intensity-value and fluorophore concentration and need to be corrected for NGS applications.

It is therefore an object of the invention to provide a method and a system, which, among others, overcomes the above mentioned problems of the prior art. In particular, one object may be to identify and solve interdependences of bead intensities across different color channels, one further object may be to identify and solve noise offsets, and one further object may be to identify and solve channel scaling.

These objects are achieved with the features of the independent claims. The dependent claims relate to further aspects of the invention.

The method according to the present invention is computer-implemented. However, it is understood by the skilled person that there are also other ways of implementing the method according to the present invention.

The invention relates to a method of intensity-bias compensation in a plurality of digital images. Preferably, the method relates to a method of intensity-bias compensation between different fluorescent compounds in a plurality of digital images. Each digital image of the plurality of digital images contains a plurality of objects, i.e. contains image information about a plurality of objects, wherein each of the plurality of objects is configured to receive at least one molecule comprising genetic information. The at least one molecule is configured to receive one of at least a first fluorescent compound and a second fluorescent compound. For example, the at least one molecule may have a cleavable fluorescent compound. A first digital image of the plurality of digital images is taken by an optical imaging system during emission of electromagnetic radiation by the first fluorescent compound and a second digital image of the plurality of digital images is taken by the optical imaging system during emission of electromagnetic radiation by the second fluorescent compound. The method comprises the following steps, preferably in the following order:

a) determining a first intensity value from the first digital image for each object;
b) determining a second intensity value from the second digital image for each object, the first and second intensity values defining data points, each data point comprising a first intensity value and a second intensity value;
c) specifying a subset of the data points;
d) determining a relation between the respective first and second intensity values on the basis of only the subset of the data points, i.e. thus determining a cross-correlation between the respective first and second intensity values; and
e) determining compensated first intensity values, i.e. cross-correlation corrected first intensity values, on the basis of the first intensity values, the second intensity values, and the relation between the respective first intensity values and the second intensity values.

For simplicity, the invention is described with respect to two intensity values. The same methodology is, however, also applicable to an arbitrary number of intensity values, which shall also be encompassed by the present invention. It may be understood that the first image and the second image contain image information of the plurality of objects. The first image may be taken such that it contains image information in a first frequency range and the second image may be taken such that it contains image information in a second frequency range. For example, the first image may be taken with a first colour filter and the second image may be taken with a second colour filter. The first intensity and the second intensity may be cross-correlated, i.e., there may be a bias between the first intensity and the second intensity. In other words, the first and second frequency ranges may overlap. This cross-correlation or cross-talk may be compensated by selecting a subset of the data points being defined by the first and second intensity values. On the basis of said subset of data points, a relation between the first and second intensity values can be determined; this given relation can be used for compensating the cross-correlation. In other words, the method may be adapted for determining original intensity values emitted by the at least one object on the basis of the intensity values determined (e.g. measured) by the optical imaging system. The cross-correlation corrected intensity values can have colour-filter specific distributions. These distributions can be determined by distinct background level and fluorophore to intensity-value mapping functions. These distributions can be characterized by selecting a subset of data-points or by using the entire set.

Characterization of the intensity distributions allows correction or normalization such that all colour-specific distributions are matching.

The at least one object may be or may comprise a single DNA/RNA strand or a group of (nearly) identical strands. The DNA/RNA strands may also be single stranded DNA/RNA fragments. Thus, genetic information comprised in the molecule received by the object may relate to the genetic information comprised in a nucleotide and/or a nucleobase. In other words, the molecule may be or may comprise a nucleotide and/or a nucleobase. Single DNA/RNA strands or groups thereof may be immobilized to the imaging object slide either directly or via beads which are commercially available, e.g., Thermo Fisher Dynabeads®. However, at least one object may also be devoid of DNA/RNA strands.

Each DNA strand may be configured to receive molecules, preferably nucleotides. The nucleotides may comprise one cleavable fluorescent compound and a cleavable cap. Furthermore, the molecules may be a plurality of four different molecules each having a fluorescent compound specific for each of the four different molecules.

The optical imaging system preferably comprises of an illumination device, e.g. an LED, to activate/stimulate the fluorescent compound(s) to excite electromagnetic radiation and a detection system, e.g. a CCD detector, to detect the emission spectra (electromagnetic radiation) of the fluorescent compound(s).

The method may be carried out over a plurality of cycles and may be applied over a defined cycle-range. Each of the plurality of cycles may be characterized in that one of the four molecules is attached to one of the DNA strands, wherein the cleavable cap ensures that only one molecule is attached to each DNA strand per cycle. After each one of the cycles, the cleavable cap may be removed so that another molecule can be attached to the DNA strand in the next cycle. At the same time, the fluorescent compound may be removed from the at least one molecule.

For each cycle, a plurality, preferably four, digital images, i.e. pictures, may be taken, one for each of the four fluorescent compounds attached to the molecules. For example, each one of the plurality of digital images may be taken with a different colour filter. Furthermore, each one of the four fluorescent compounds may have one of a main emission spectrum in the red, blue, yellow or green spectral regime.

The relation between the first and second intensity values may be a mathematical function.

For example, the mathematical function may be a function of the determined first and second intensity values (i.e. the measured intensity values) and may result in first and second original (i.e. emitted) intensity values. The mathematical function may for example be written in terms of a cross-talk matrix.

For example, under the assumption that the emission spectra of all fluorophores are perfectly separated such that no cross-talk exists, the intensity value detected in/for a given channel ($I_0$) would be determined by the concentration of the matching fluorophore ($c_0$) ($I_0=g(c_0)$). Fluorophore intensities are typically linearly dependent on the concentration, which simplifies the previous function to $I_0 \propto c_0$, such that the measured intensity could be used as a proxy for the fluorophore concentration. If, however, cross-talk between channels exists, the measured intensity value $I_c$ for a channel c is influenced by the concentration of non-matching fluorophores ($I_c=g(I_0, I_1 \ldots I_n)$). Typically, contributions may be additive and linear, which may allow to write the contribution of all channel intensities to the channel of interest as $I_c=\beta_{c,0}(I_0)+\beta_{c,1}+ \ldots +\beta_{c,n}(c_n))$, where $\beta_{c,i}$ denotes the linear contribution of channel i to the channel of interest (c). A set of n analogous equations can describe the cross-talk influence for all n channels. The contribution parameters can be conveniently described in a n×n cross-talk matrix:

$$\begin{pmatrix} \beta_{0,0} & \cdots & \beta_{0,n} \\ \vdots & \ddots & \vdots \\ \beta_{n,0} & \cdots & \beta_{n,n} \end{pmatrix}$$

By applying the described method, the cross-talk of determined intensity values can be compensated and unbiased intensity values can be determined.

Preferably, the method further comprises the following steps:
f) determining noise offsets on the basis of the first and second intensity values; and
g) subtracting the determined noise offsets from the first and second intensity values.

In other words, the noise offset may be determined on the basis of a background intensity signal. Thus, the method may also be adapted for compensating channel-specific intensity biases. For example, a first noise offset may be determined on the basis of the first intensity values and a second noise offset may be determined on the basis of the second intensity values. In other words, channel-specific noise offset may be determined on the basis of channel-specific background intensity signals. In this way, noise offset, preferably channel-specific noise offset, may be compensated. The determined noise offset values may either be subtracted from the first and second intensity values determined in steps a) and b) and/or from the compensated intensity values determined in step e).

The detected intensity $I_c$ values for a given channel c can be understood as the convolved signal of the contributing fluorophore concentration (see above) with an additional channel-specific noise $I_c = \beta_{c,0}(I_0) + \beta_{c,1}(c_0) + \ldots + \beta_{c,n}(c_n) + \varepsilon_c$, where $\varepsilon_c$ denotes the noise component. The noise component for all measured intensities of a given channel may be modelled by a random variable. The first mode of this random variable may be channel-specific and may be non-zero. It may be preferable to correct/compensate the observed intensities by translating these intensities such that the mode of the noise component may have a specific value, for example zero.

To quantify the mode of the noise component, objects with no expected signal component may be measured. These may be objects without attached DNA/RNA strands (empty beads) or objects with attached DNA/RNA. In the latter case, noise estimation for channel c may be performed on objects which emit in channel k, distinct to channel c. Potential crosstalk may be eliminated by the correction described above or by choosing a c and k such that no crosstalk is observed. The noise-offset correction can be conveniently integrated into a (n+1×n+1) cross talk matrix, where n equals the number of channels and $\varepsilon'_n$ the channel-specific noise offset:

$$\begin{matrix} \beta_{0,0} & \cdots & \beta_{0,n} & 0 \\ \vdots & \ddots & \vdots & 0 \\ \beta_{n,0} & \cdots & \beta_{n,n} & 0 \\ \varepsilon'_0 & \cdots & \varepsilon'_n & 1 \end{matrix}$$

Preferably, the method further comprises the following steps:
h) determining a first intensity distribution for the first intensity values and a second intensity distribution for the second intensity values;
i) determining a scaling function between the first intensity distribution and the second intensity distribution;
j) rescaling the first and/or second intensity values with the scaling function.

The scaling function may include scaling factors or may consist of scaling factors.

In other words, it may be understood that channel-specific intensity distributions are determined. Thus, the method may also be adapted for compensating channel-specific intensity biases. In this way, channel-specific intensity distributions, i.e. channel scaling, may be compensated. In step j), the first and/or second intensity values determined in step a) and b), the compensated intensity values determined in step e), and/or the intensity values including subtracted noise component determined in step g) may be rescaled.

The detected intensity values may have different distribution for different channels. These may be due to fluorophore specific emission properties or may be due to distinct detection capabilities. Channel-specific intensity distributions may be measured on a subset of objects which emit in a given channel. Distributions may be characterized by determining summary statistics (e.g. mean, median, etc) or by fitting a probabilistic model to the data. Distinct channel-specific distributions may be collapsed to a common distribution, thereby correcting for this bias. If this collapsing method can be performed by a linear factor this factor can be stored as the diagonal component in the cross-talk matrix.

Preferably, the method comprises the step of determining compensated first intensity values and compensated second intensity values on the basis of the first intensity values, the second intensity values, and the relation between the first intensity values and the second intensity values.

In other words, the method may comprise the step of determining original or emitted intensity values on the basis of the determined intensity values.

Preferably, specifying the subset of data points is performed by selecting a region of interest in the first and second digital images. In other words, corresponding regions of interest, for example a centre region, may be selected in the first and second digital images.

In this way, it is not necessary to process all intensity values of all objects. Thus, computing power can be saved. Moreover, the region of interest can, e.g., be selected in the brightest region of the digital image. In this way, the relation can be determined more precisely.

Preferably, the method is repeatedly carried out in a plurality of cycles, wherein specifying the subset of data points is performed by selecting one or more cycles of the plurality of cycles. In other words, a number of cycles of the plurality of cycles may be specified. Thus, the subset of data points may only comprise intensity values of the selected cycles.

In this way, for example, the relation between the first and second intensity values may first be determined in the selected cycles and may then be used for the cross-compensation in the subsequent cycles.

Preferably, the method further comprises the following step, preferably after step c), more preferably between steps c) and d):
k) grouping the subset of the data points into a plurality of groups, wherein each group of the plurality of groups comprises one representative data point.

Furthermore, determining the relation between the first and second intensity values is performed on the basis of only the representative data points.

In other words, the subset of data points may be grouped into bins, i.e., the subset of data points may be binned. Each bin may contain a plurality of data points. In this way, the number of data points used for determining the relation between the first and second intensity values may be reduced, thereby reducing the computing power necessary for carrying out the method. Furthermore, grouping the data points into bins may also compensate for outliers in the subset of data points.

Preferably, the subset of the first and second intensity values is performed by separating the subset of the first and second intensity values into bins with fixed borders. In other words, each bin may contain intensity values lying within a predefined range of intensity values. Thus, the borders of the bins may be predefined and the number of data points being represented by one bin may depend on the predefined borders. In this way, the method may become more robust.

Preferably, grouping the subset of the first and second intensity values is performed by separating the subset of the first and second intensity values into bins having a fixed number of data points. In other words, the number of data points may be specified for each bin and the borders of the bins may be adjusted dynamically. In this way, it can be ensured that there are enough data points in each bin.

Preferably, determining the relation between the first and second intensity values is performed with a polynomial fitting method. Preferably, the polynomial fitting method may only have a degree of 1.

Preferably, determining the relation between the first and second intensity values is performed with a random sample consensus algorithm. The random sample consensus algorithm may also be denoted as RANSAC algorithm. The RANSAC algorithm may be less susceptible to outliers in the subset of data points. Thus, a more reliable relation between the first and second intensity values may be obtained.

Preferably, the method further comprises the following step, preferably between steps d) and e):
l) determining a cross-talk matrix on the basis of the relation between the first and second intensity values.

The cross-talk matrix A may be a matrix describing the linear relation between the emitted intensity values e and the determined (i.e. measured) intensity values d. The vectors e and d of length n may contain intensity values for all channels n. For example, the determined intensity values may be written in terms of the emitted intensity values as follows:

$$d = e * A$$

$d_i$ being the $i^{th}$ determined intensity values, $e_j$ the $j^{th}$ emitted intensity value, and $A_{ij}$ the matrix entry describing the relation between $d_i$ and $e_j$. Thus, the emitted intensity values (i.e. the compensated intensity values) can be determined by means of the inverted matrix $A^{-1}$:

$$e = d * A^{-1}$$

For example, if the main overlap is between the blue (i=0) and red (i=1) fluorescent spectrum, the cross-talk matrix may receive an entry in the order of the respective determined crosstalk (e.g. $A_{0,1}=0.4$) for the relation between intensity values for the blue spectrum (e.g. the digital image being taken with a green filter) and the intensity values for the red spectrum (e.g. the digital image being taken with a yellow filter). The other non-diagonal entries of the matrix may be considerably smaller. This, however, may depend on the filter setup used.

Preferably, the subset of data points only comprises intensity values of objects having received a molecule comprising genetic information. In other words, the subset of data points may only comprise intensity values of live-beads. In this way, the result may be dominated by signal intensities and not by background intensities.

Another aspect of the invention relates to a system being configured to perform any one of the aforementioned methods.

Another aspect of the invention relates to a system for cross-talk compensation in at least a first digital image and a second digital image, wherein each digital image of the at least first and second digital images contains image information about a plurality of objects. Furthermore, each of the plurality of objects is configured to receive at least one molecule comprising genetic information. The at least one molecule is configured to receive one of at least a first fluorescent compound and a second fluorescent compound. The first digital image is taken by an optical imaging system during emission of electromagnetic radiation by the first fluorescent compound and the second digital image being taken by the optical imaging system during emission of electromagnetic radiation by the second fluorescent compound. The system comprises:
i) an intensity determination unit configured for determining a first intensity value from the first digital image for each object and a second intensity value from the second digital image for each object, the first and second intensity values defining data points, each data point comprising a first intensity value and a second intensity value;
ii) a subset determination unit configured for specifying a subset of the data points;
iii) a cross-talk compensation unit configured for determining a relation between the respective first and second intensity values on the basis of only the subset of the data points, i.e. thus determining a cross-correlation between the respective first and second intensity values, and for determining compensated first intensity values, i.e. cross-correlation corrected first intensity values, on the basis of the first intensity values, the second intensity values, and the relation between the first intensity values and the second intensity values.

Preferably, the system further comprises:
iv) a noise-offset compensation unit configured for determining noise offsets on the basis of the first and second intensity values and subtracting the determined noise offsets from the first and second intensity values.

Preferably, the system further comprises:
v) an intensity-scaling compensation unit configured for determining a first intensity distribution for the first intensity values and a second intensity distribution for the second intensity values, determining a scaling function between the first intensity distribution and the second intensity distribution, and rescaling the first and/or second intensity values with the scaling function.

It is to be understood that the embodiments disclosed herein which relate to a method, also relate to a system comprising means adapted for carrying out the respective method steps. Therefore, the definitions, explanations, effects, and examples given with respect to the method also describe a corresponding system.

Yet another aspect of the invention relates to a computer program product comprising one or more computer readable media having computer executable instructions for performing the steps of the method described in the context of the present invention.

Some exemplary embodiments are now described with reference to the drawings. For explanation purpose, various specific details are set forth, without departing from the scope of the present invention as claimed.

DETAILED DESCRIPTION OF EXEMPLARY EMBODIMENTS

Figure 1:
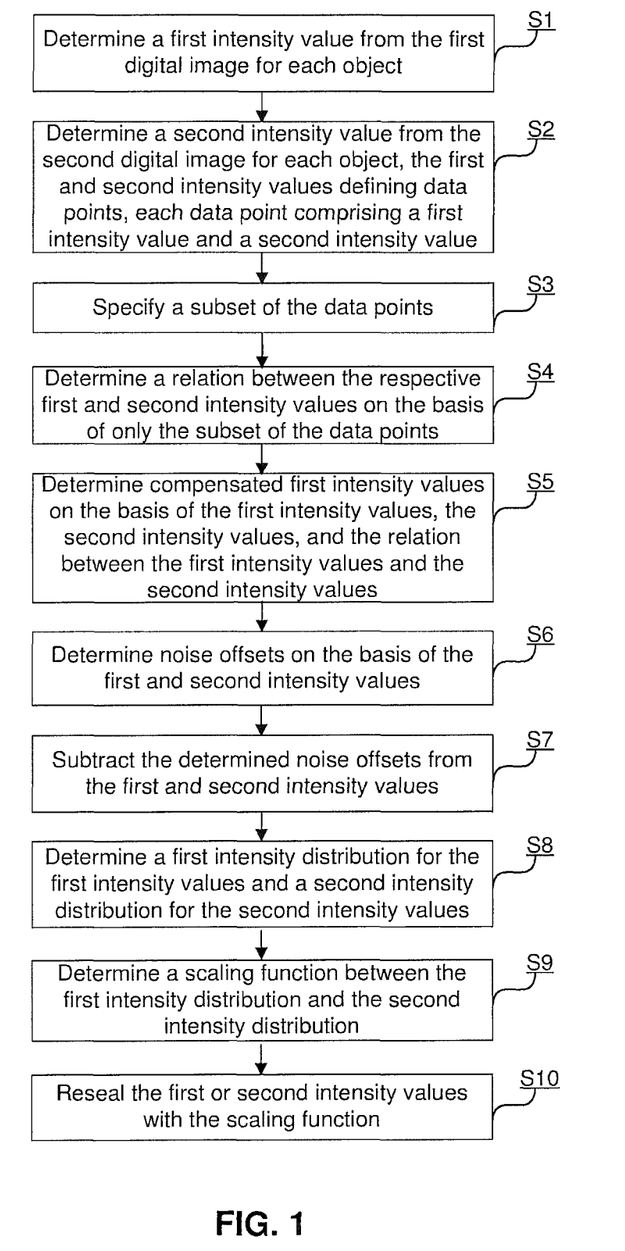
FIG. 1 illustrates a method according to an exemplary embodiment of the invention.

FIG. 1 illustrates a method according to an exemplary embodiment of the invention. The method is adapted for compensating intensity biases and in particular cross talk effects in a plurality of digital images. Each digital image of the plurality of digital images contains a plurality of objects, wherein each of the plurality of objects is configured to receive at least one molecule comprising genetic information. The at least one molecule is configured to receive one of at least a first fluorescent compound and a second fluorescent compound. A first digital image of the plurality of digital images is taken by an optical imaging system during emission of electromagnetic radiation by the first fluorescent compound and a second digital image of the plurality of digital images is taken by the optical imaging system during emission of electromagnetic radiation by the second fluorescent compound. The method comprises the following steps, preferably in the following order:
   S1: determining a first intensity value from the first digital image for each object;
   S2: determining a second intensity value from the second digital image for each object, the first and second intensity values defining data points, each data point comprising a first intensity value and a second intensity value;
   S3: specifying a subset of the data points;
   S4: determining a relation between the respective first and second intensity values on the basis of only the subset of the data points; and
   S5: determining compensated first intensity values on the basis of the first intensity values, the second intensity values, and the relation between the first intensity values and the second intensity values.

According to an exemplary embodiment of the invention, the method may further comprise the following steps:
   S6: determining noise offsets on the basis of the first and second intensity values; and
   S7: subtracting the determined noise offsets from the first and second intensity values.

According to an exemplary embodiment of the invention, the method may further comprising the following steps:
   S8: determining a first intensity distribution for the first intensity values and a second intensity distribution for the second intensity values;
   S9: determining a scaling function between the first intensity distribution and the second intensity distribution;
   S10: rescaling the first and/or second intensity values with the scaling function.

According to an exemplary embodiment of the invention, the subset of data points is specified (step S3) by selecting a region of interest in the first and second digital images. However, the subset may also alternatively or additionally be specified by selecting one or more cycles of the plurality of cycles as described in more detail with respect to FIG. 6.

According to an exemplary embodiment of the invention, the relation between the first and second intensity values and the noise-offset is expressed in form of a cross-talk matrix, i.e. the cross-talk matrix is determined on the basis of the relation between the first and second intensity values. As described before, the (n+1×n+1) cross-talk matrix A, where n equals the number of channels may be written as $$\begin{matrix} \beta_{0,0} & \cdots & \beta_{0,n} & 0 \\ \vdots & \ddots & \vdots & 0 \\ \beta_{n,0} & \cdots & \beta_{n,n} & 0 \\ \varepsilon'_0 & \cdots & \varepsilon'_n & 1 \end{matrix}$$

A vector of emitted intensity values (e) of length n may be gained by multiplying a vector of determined intensity values (d) of length n+1 ($d_{n+1}=1$) with the cross talk matrix A:

$$d = e * A$$

Thus, the emitted intensity values (i.e. the compensated intensity values) can be determined by means of the inverted matrix $A^1$:

$$e = d * A^{-1}$$

According to a further exemplary embodiment of the invention, the method is further adapted for determining compensated first and second intensity values on the basis of the first and second intensity values as well as the relation between the first and second intensity values.

Moreover, in the method, only objects having received a molecule with genetic information may be selected, i.e., the subset of data points may only comprise intensity values of objects that have received such a molecule.

Figure 2:
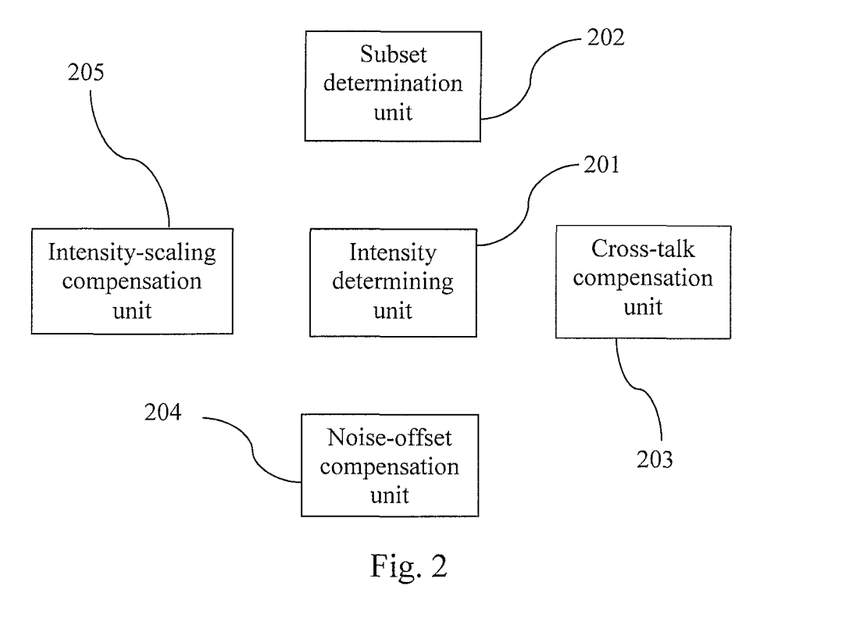
FIG. 2 illustrates a system according to an exemplary embodiment of the invention.

FIG. 2 illustrates a system according to the present invention. The system comprises an intensity determination unit 201, a subset determination unit 202, and a cross-talk compensation unit 203.

According to an exemplary embodiment, the system may further comprise a noise-offset compensation unit 204. According to another exemplary embodiment, the system may further comprise an intensity-scaling compensation unit 205. All of these units are configured to execute one or more of the steps of the present invention. While the present invention is described using independent units 201, 202, 203, 204, 205 it is apparent that the independent units can also be part of one single unit as long as the steps of the present invention are executed.

The intensity determination unit 201 is configured for determining a first intensity value for each object from the first digital image and a second intensity value for each object from the second digital image. Thus, for each object, a first and second intensity value may be determined. However, it may be possible that a first and/or second intensity value is not determined for some objects, e.g., because one object is lost.

The subset determination unit 202 receives the determined first and second intensity values. It may be understood that the first and second intensity values come in pairs and that each pair of first and second intensity values defines a data point. Furthermore, the subset determination unit 202 is configured for specifying a subset of the data points. This may be carried out as described in the context of the present invention.

The cross-talk compensation unit 203 receives the subset of the intensity values. On the basis of said subset, the cross-talk compensation unit 203 determines a relation between the first and second intensity values. This may, e.g., be carried out as described in the context of the present invention. Furthermore, the cross-talk compensation unit 203 is configured for determining compensated first intensity values on the basis of the first intensity values, the second intensity values, and the relation between the first intensity values and the second intensity values.

According to an exemplary embodiment of the invention, the cross-talk compensation unit 203 also receives the determined first and second intensity values and determines compensated first intensity values on the basis of the first intensity values, the second intensity values, and the relation between the first and second intensity values.

The noise-offset compensation unit 204 receives a subset of the intensity values. The intensity values may be received from the intensity determination unit 201 or from the cross-talk compensation unit 203. The subset may be the same or a distinct subset received by the cross-talk compensation unit. The noise-offset compensation unit is configured to determine the channel-specific noise offset values and compensate for this offset.

The channel-scaling compensation unit 205 receives a subset of intensity values. The intensity values may be received from the intensity determination unit 201, the cross-talk compensation unit 203 or the noise-offset compensation unit 204. The channel-scaling compensation unit is configured to determine the channel-specific intensity value distribution and compensate for distinct distributions.

The functionality of the intensity determination unit 201, the subset determination unit 202, the cross-talk compensation unit 203, the noise-offset compensation unit 204, and the channel-scaling compensation unit 205 is further described in terms of method steps in the in the exemplary embodiments of the present invention. It is obvious for a person skilled in the art that the following description of method steps gives rise to corresponding functions of the intensity determination unit 201, the subset determination unit 202, the cross-talk compensation unit 203, the noise-offset compensation unit 204, and the channel-scaling compensation unit 205 or a further unit.

Figure 3:
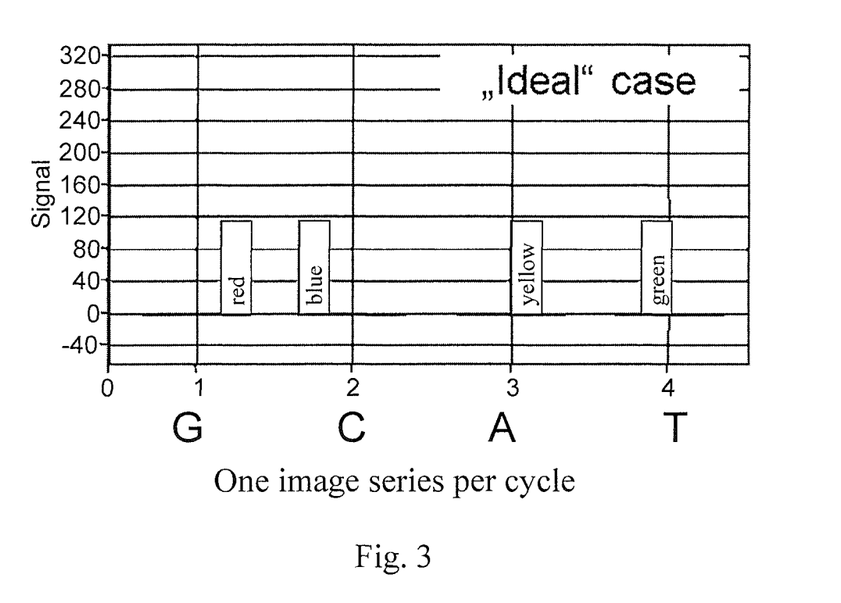
FIG. 3 illustrates an ideal signal of the different channels.

FIG. 3 shows the signal strength determined from four cycles for one bead. Each of the cycles comprises four images, wherein FIG. 3 illustrates the signal strength for the respective channels G, C, A, T, i.e. the base call for that specific cycle. That is, in an ideal case each channel would provide a single signal for each channel. However, due to different parasitic effects, like auto-fluorescence effects and cross-talk effects between different channels, the signals for the different channels are most likely to be different from the ideal case.

Figure 4:
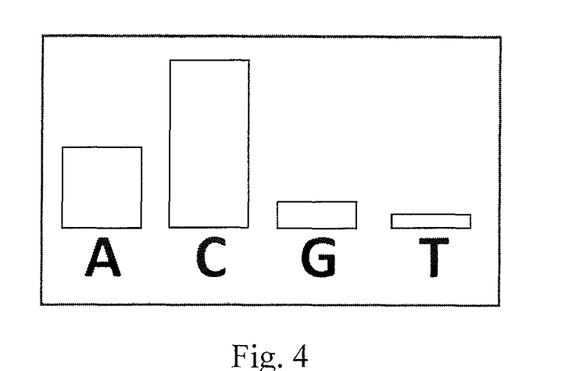
FIG. 4 illustrates cross-talk effects between the different channels.

FIG. 4 illustrates an exemplary cross-talk effect. In comparison to the ideal case illustrated by FIG. 3, not only the main signal has a value different from zero but also the other channels show non-zero values, due to overlapping fluorescent spectra. That is, due to an overlap in the dye (fluorescent compound) emission frequencies an interdependency between pairs of color channels can be observed (cross-talk). Consequently, bead intensities are inherently biased. This crosstalk between different channels is compensated with the method and system described in the context of the present invention.

Figure 5:
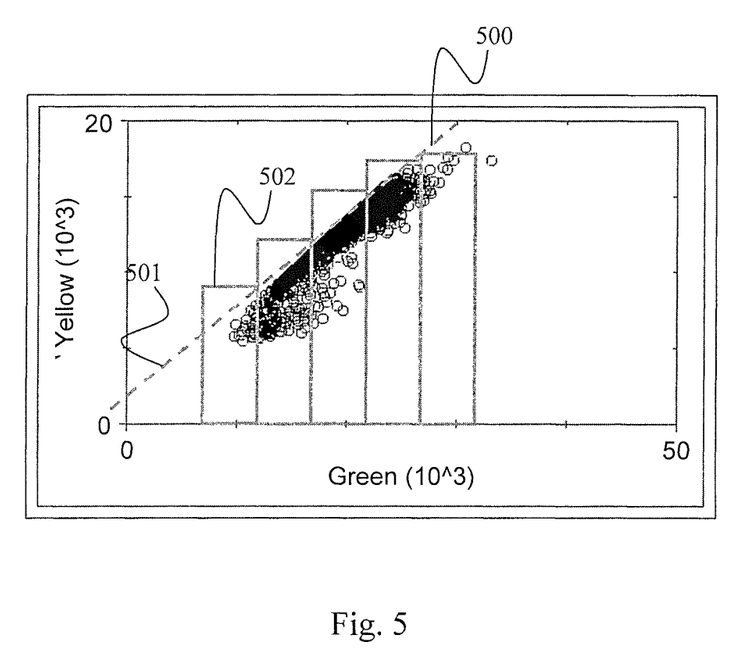
FIG. 5 illustrates the interdependence of intensity values between two different channels.

FIG. 5 also illustrates an exemplary cross-talk effect. In the diagram of FIG. 5, the first intensity values are plotted against the second intensity values. In this example, the first intensity values correspond to the intensities of the yellow channel and the second intensity values correspond to the intensities of the green channel. Each point 500 in the diagram corresponds to a data point, i.e. a pair of first and second intensity values. The relation between the first and second intensity values is exemplarily shown with the dashed line 501. According to exemplary embodiments, this relation is determined with a polynomial fitting method or a RANSAC algorithm. For this purpose, the data points may be grouped into a plurality of groups, wherein each group is represented by one data point. I.e., the data points can be grouped into bins 502. These bins are then used for determining the relation between the first and second intensity values. According to exemplary embodiments of the invention, the bins 502 are bins with fixed borders or bins with a fixed number of data points.

Figure 6:
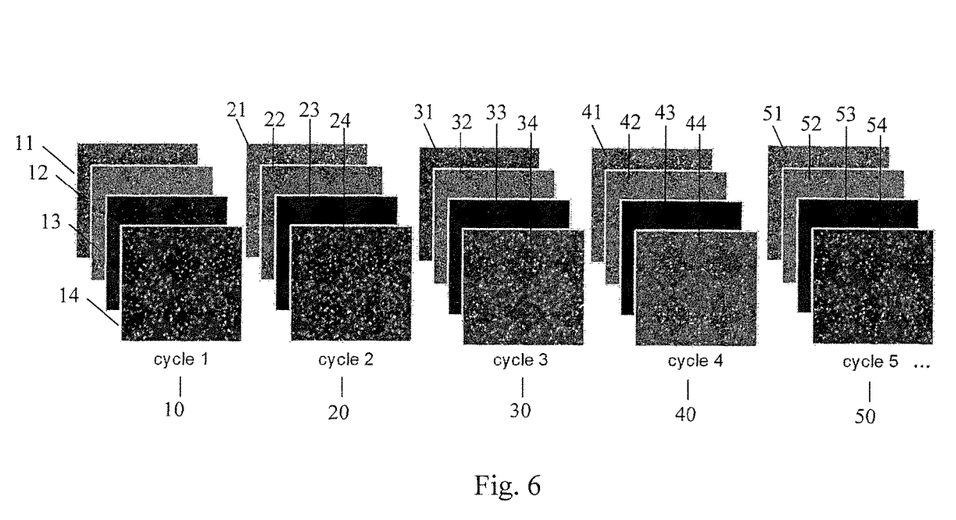
FIG. 6 illustrates the images taken in different cycles according to an embodiment of the present invention.

FIG. 6 illustrates the images 11-14, 21-24, 31-34, 41-44, 51-54 taken in a plurality of cycles 10-50 of the method. This illustration should not be construed as limiting as of the amount of images taken in a corresponding cycle or the amounts of cycles. As can be seen in FIG. 6 in each of the cycles 10-50 four images 11-14, 21-24, 31-34, 41-44, 51-54 are taken, i.e. acquired, captured etc., in this example. In particular, each of the four images 11-14, 21-24, 31-34, 41-44, 51-54 in one cycle 10-50 corresponds to one channel of the optical imaging system, i.e. red, green, yellow and blue. For example, every first image may be taken with a first color filter, every second image with a second color filter, every third image with a third color filter, and every fourth image with a fourth color filter. The different colors are emitted by fluorescent compounds carried by different molecules which are received by DNA strands attached to the objects (beads). More particular, each of the different fluorescent compounds represents one of a specific DNA base, i.e. thymine (T), adenine (A), cytosine (C), and guanine (G). For example, the fluorescent compounds are associated to the DNA bases as follows: T=green; A=yellow; C=blue; and G=red.

In each cycle 10-50 the first images 11, 21, 31, 41, 51 corresponds to one of the four channels T, A, C, G, e.g. G. The second images 12, 22, 32, 42, 52 then correspond to a second one of the remaining three channels T, A, C, e.g. C. The third images 13, 23, 33, 43, 53 then correspond to a third one of the remaining two channels T, A, e.g. A. The fourth images 14, 24, 34, 44, 54 then correspond to a fourth one of the remaining channel, e.g. T.

According to an exemplary embodiment of the invention, the subset may be specified in that only first and second intensity values of a given number of cycles, e.g. of cycles 10-30, are selected.

Figure 7:
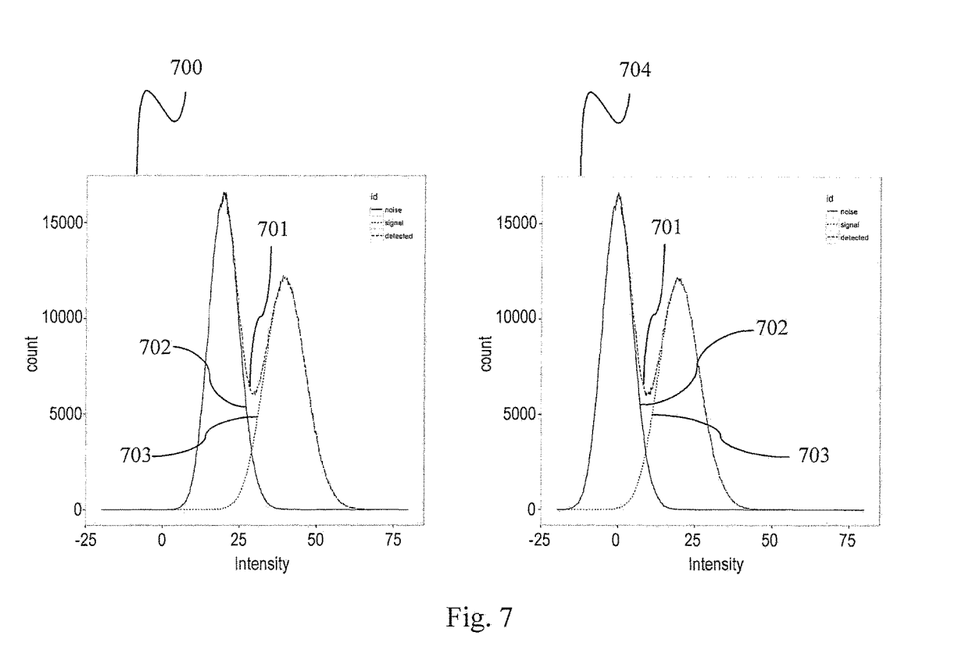
FIG. 7 illustrates noise-offset effects and their correction according to an embodiment of the invention.

FIG. 7 illustrates noise-offset effects and their correction according to an exemplary embodiment of the invention. The graph 700 shows the distribution of detected intensities 701 as well as the contributors to the detected intensities (noise: 702, signal: 703). Distributions are visualized as count vs. intensity plots for a plurality of measured objects, wherein the x-axis indicates the intensity and the y-axis the number of objects at a given intensity. The noise-offset correction method identifies the first mode of the noise signal in the input intensity distribution (graph 700) and corrects the detected intensity such that this mode is aligned with a specified value (graph 704). For this visualization the specified value was set to 0. Performing noise-offset correction for each channel individually allows the specification of a common noise-offset for all channels. The first mode of the noise signal may be detected by a data driven approach, by probabilistic modeling of the noise or by another method.

Figure 8:
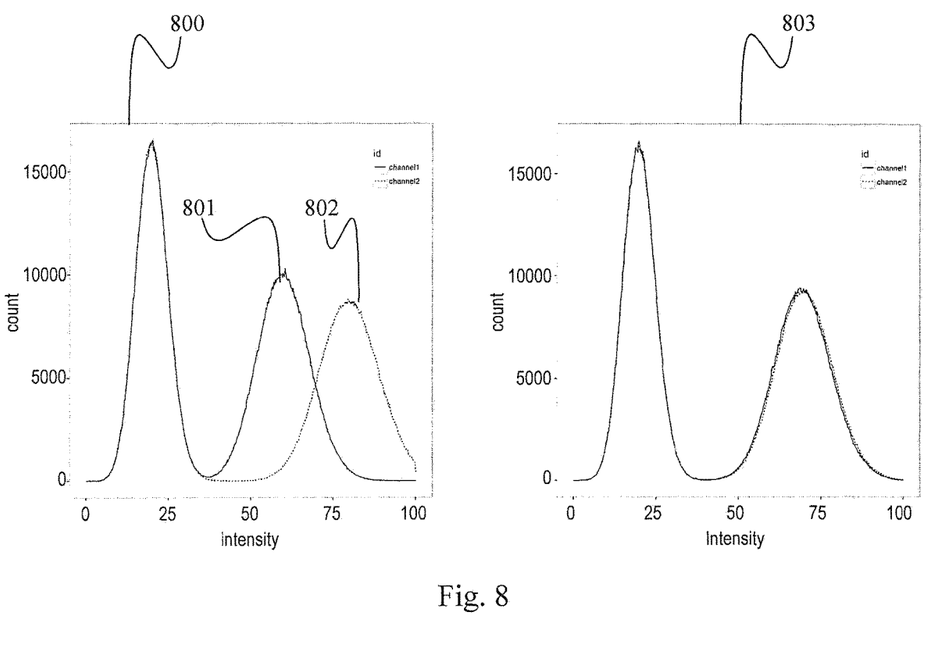
FIG. 8 illustrates channel-scaling effects and their correction according to an embodiment of the invention.

FIG. 8 illustrates channel-scaling effects and their correction according to an exemplary embodiment of the invention. The graph 800 shows the distribution of detected intensities for two channels (channel 1: 801, channel 2: 802). Distributions are visualized as count vs. intensity plots for a plurality of measured objects, wherein the x-axis indicates the intensity and the y-axis the number of objects at a given intensity. Different channels may have distinct signal intensity distributions as shown in the left graph 800. The channel-scaling correction characterizes the channel-specific intensity distributions and corrects them such that all channel intensity distribution collapse to a common one (right graph 803). The intensity distribution characterization may be performed by a probabilistic model or by another method. If the correction can be performed by a linear transform the channel-scaling correction can be performed via the diagonal components of the cross-talk matrix described herein. A non-linear transform may be corrected by another method.

The forgoing method steps and the system of the exemplary embodiments have been described as relating to DNA/RNA sequencing. However, as it will be apparent to the person skilled in the art the present invention is not restricted to this technical field. It is clear that the solution of the present invention can be applied to numerous other technical fields, where fluorescent images comprising different types of objects are analyzed. That is, the objects do not have to be beads, but can also be any kind of fluorescent emitting objects.

As the present invention may be embodied in several forms without departing from the scope or essential characteristics thereof, it should be understood that the above-described embodiments are not limited by any of the details of the foregoing descriptions, unless otherwise specified, but rather should be construed broadly within the scope as defined in the appended claims, and therefore all changes and modifications that fall within the present invention are therefore intended to be embraced by the appended claims.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively.

The invention claimed is:

1. A method of cross-talk compensation in a plurality of digital images, wherein:
    each digital image of the plurality of digital images contains image information about a plurality of objects, each of the plurality of objects being configured to receive at least one molecule comprising genetic information,
    the at least one molecule being configured to receive one of at least a first fluorescent compound and a second fluorescent compound,
    a first digital image of the plurality of digital images being taken by an optical imaging system during emission of electromagnetic radiation by the first fluorescent compound, and
    a second digital image of the plurality of digital images being taken by the optical imaging system during emission of electromagnetic radiation by the second fluorescent compound,
    wherein the method comprises:
        determining a first intensity value from the first digital image for each object;
        determining a second intensity value from the second digital image for each object, the first and second intensity values defining data points, each data point comprising the first intensity value and the second intensity value;
        specifying a subset of the data points;
        in response to the specifying the subset of the data points, grouping the subset of the data points into a plurality of groups with fixed borders or having a fixed number of data points, wherein each group of the plurality of groups comprises one representative data point;
        determining a cross-correlation between the first and second intensity values based on the plurality of groups using a polynomial fitting method or a random sample consensus algorithm; and
        determining compensated intensity values based on the first intensity values, the second intensity values, and the cross-correlation between the first intensity values and the second intensity values.

2. The method of claim 1, further comprising:
    determining noise offsets based on the first and second intensity values; and
    subtracting the determined noise offsets from the first and second intensity values.

3. The method of claim 1, further comprising:
    determining a first intensity distribution for the first intensity values and a second intensity distribution for the second intensity values;
    determining a scaling function between the first intensity distribution and the second intensity distribution; and
    rescaling the first or second intensity values with the scaling function.

4. The method of claim 1, wherein the specifying the subset of the data points further comprises:
    specifying the subset of the data points by receiving a selection of a region of interest in the first and second digital images.

5. The method of claim 1, further comprising:
    determining a cross-talk matrix based on the cross-correlation between the first and second intensity values.

6. The method of claim 1, wherein the determining the cross-correlation comprises determining the cross-correlation between the first and second intensity values for only the representative data points.

7. A system for cross-talk compensation in at least a first digital image and a second digital image, wherein:
    each digital image of the at least first and second digital images contains a plurality of objects, each of the plurality of objects being configured to receive at least one molecule comprising genetic information,
the at least one molecule being configured to receive one of at least a first fluorescent compound and a second fluorescent compound,
the first digital image being taken by an optical imaging system during emission of electromagnetic radiation by the first fluorescent compound, and
the second digital image being taken by the optical imaging system during emission of electromagnetic radiation by the second fluorescent compound,
the system comprising:
a memory; and
at least one processor coupled to the memory and configured to:
determine a first intensity value from the first digital image for each object;
determine a second intensity value from the second digital image for each object, the first and second intensity values defining data points, each data point comprising the first intensity value and the second intensity value;
specify a subset of the data points;
in response to the specifying the subset of the data points, group the subset of the data points into a plurality of groups with fixed borders or having a fixed number of data points, wherein each group of the plurality of groups comprises one representative data point;
determine a cross-correlation between the first and second intensity values based on the plurality of groups using a polynomial fitting method or a random sample consensus algorithm; and
determine compensated intensity values based on the first intensity values, the second intensity values, and the cross-correlation between the first intensity values and the second intensity values.

8. The system of claim 7, wherein the at least one processor is further configured to:
determine noise offsets based on the first and second intensity values; and
subtract the determined noise offsets from the first and second intensity values.

9. The system of claim 7, wherein the at least one processor is further configured to:
determine a first intensity distribution for the first intensity values and a second intensity distribution for the second intensity values;
determine a scaling function between the first intensity distribution and the second intensity distribution; and
rescale the first or second intensity values with the scaling function.

10. The system of claim 7, wherein to specify the subset of the data points, the at least one processor is further configured to:
specify the subset of the data points by receiving a selection of a region of interest in the first and second digital images.

11. The system of claim 7, wherein the at least one processor is further configured to:
determine a cross-talk matrix based on the cross-correlation between the first and second intensity values.

12. The system of claim 7, wherein to determine the cross-correlation, the at least one processor is further configured to determine the cross-correlation between the first and second intensity values for only the representative data points.

13. A computer program product comprising a non-transitory computer readable medium, wherein:
each digital image of a plurality of digital images contains image information about a plurality of objects,
each of the plurality of objects being configured to receive at least one molecule comprising genetic information,
the at least one molecule being configured to receive one of at least a first fluorescent compound and a second fluorescent compound,
a first digital image of the plurality of digital images being taken by an optical imaging system during emission of electromagnetic radiation by the first fluorescent compound, and
a second digital image of the plurality of digital images being taken by the optical imaging system during emission of electromagnetic radiation by the second fluorescent compound,
wherein the non-transitory computer readable medium comprises computer executable instructions for performing the following steps:
determining a first intensity value from the first digital image for each object;
determining a second intensity value from the second digital image for each object, the first and second intensity values defining data points, each data point comprising the first intensity value and the second intensity value;
specifying a subset of the data points;
in response to the specifying the subset of the data points, grouping the subset of the data points into a plurality of groups with fixed borders or having a fixed number of data points, wherein each group of the plurality of groups comprises one representative data point;
determining a cross-correlation between the first and second intensity values based on the plurality of groups using a polynomial fitting method or a random sample consensus algorithm; and
determining compensated intensity values based on the first intensity values, the second intensity values, and the cross-correlation between the first intensity values and the second intensity values.

14. The computer program product of claim 13, wherein the non-transitory computer readable medium further comprises computer executable instructions for performing the following steps:
determining noise offsets based on the first and second intensity values; and
subtracting the determined noise offsets from the first and second intensity values.

15. The computer program product of claim 13, wherein the non-transitory computer readable medium further comprises computer executable instructions for performing the following steps:
determining a first intensity distribution for the first intensity values and a second intensity distribution for the second intensity values;
determining a scaling function between the first intensity distribution and the second intensity distribution; and
rescaling the first or second intensity values with the scaling function.

16. The computer program product of claim 13, wherein the specifying comprises:
specifying the subset of the data points by receiving a selection of a region of interest in the first and second digital images.

17. The computer program product of claim 13, wherein the determining the cross-correlation comprises determining the cross-correlation between the first and second intensity values for only the representative data points.

* * * * *